US010085618B2

(12) United States Patent
Komuro

(10) Patent No.: US 10,085,618 B2
(45) Date of Patent: Oct. 2, 2018

(54) TREATMENT TOOL EXCHANGING DEVICE AND MEDICAL SYSTEM

(71) Applicant: OLYMPUS CORPORATION, Tokyo (JP)

(72) Inventor: Takahiro Komuro, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 602 days.

(21) Appl. No.: 14/865,524

(22) Filed: Sep. 25, 2015

(65) Prior Publication Data

US 2016/0058269 A1 Mar. 3, 2016

Related U.S. Application Data

(63) Continuation of application No. PCT/JP2014/052068, filed on Jan. 30, 2014.
(Continued)

(51) Int. Cl.
*A61B 1/00* (2006.01)
*A61B 1/005* (2006.01)
(Continued)

(52) U.S. Cl.
CPC ........ *A61B 1/00133* (2013.01); *A61B 1/0016* (2013.01); *A61B 1/0052* (2013.01);
(Continued)

(58) Field of Classification Search
CPC . A61B 1/00133; A61B 1/0016; A61B 1/0052; A61B 1/0125; A61B 1/018;
(Continued)

(56) References Cited

U.S. PATENT DOCUMENTS

| 2005/0090709 A1 | 4/2005 | Okada et al. |
| 2008/0064921 A1 | 3/2008 | Larkin et al. |
| 2010/0228265 A1 | 9/2010 | Prisco |

FOREIGN PATENT DOCUMENTS

| CN | 101219062 A | 7/2008 |
| JP | 2003-520057 A | 7/2003 |

(Continued)

OTHER PUBLICATIONS

Chinese Office Action dated Dec. 2, 2016 in related Chinese Patent Application No. 201480017633.1.
(Continued)

*Primary Examiner* — Jonathan Miles
*Assistant Examiner* — George J Ulsh
(74) *Attorney, Agent, or Firm* — Scully, Scott, Murphy & Presser, P.C.

(57) ABSTRACT

Provided is a treatment tool exchanging device that switches and holds a plurality of treatment tools for treating a target to be treated. The treatment tool exchanging device includes a flexible insertion part into which the plurality of treatment tools are inserted and in which a plurality of treatment tool channels for defining insertion paths for the treatment tools are formed, a driving part that advances each of the plurality of treatment tools, a manipulating part that manipulates the plurality of treatment tools to perform treatment, and a control unit that controls the amount of protrusion, from the treatment tool channel of the treatment tool, which has protruded from a distal end of the treatment tool channel, among the plurality of treatment tools. The insertion part has a switching part that changes the insertion path of the treatment tool to be inserted.

4 Claims, 17 Drawing Sheets

Related U.S. Application Data

(60) Provisional application No. 61/806,128, filed on Mar. 28, 2013.

(51) Int. Cl.
*A61B 1/012* (2006.01)
*A61B 1/018* (2006.01)
*A61B 19/00* (2006.01)
*A61B 34/37* (2016.01)
*A61B 17/29* (2006.01)
*A61B 17/34* (2006.01)
*A61B 34/30* (2016.01)

(52) U.S. Cl.
CPC .......... *A61B 1/018* (2013.01); *A61B 1/0125* (2013.01); *A61B 19/2203* (2013.01); *A61B 34/30* (2016.02); *A61B 34/37* (2016.02); *A61B 2017/2906* (2013.01); *A61B 2017/3445* (2013.01); *A61B 2019/2211* (2013.01); *A61B 2019/2223* (2013.01); *A61B 2034/301* (2016.02)

(58) Field of Classification Search
CPC . A61B 34/30; A61B 34/37; A61B 2017/2906; A61B 2017/3445; A61B 2034/301
See application file for complete search history.

(56) References Cited

FOREIGN PATENT DOCUMENTS

| | | |
|---|---|---|
| JP | 2007-105398 A | 4/2007 |
| JP | 2008-188109 A | 8/2008 |
| JP | 2010-511440 A | 4/2010 |
| WO | WO 00/24320 A1 | 5/2000 |
| WO | 2008/070556 A1 | 6/2008 |
| WO | WO 2011/070846 A1 | 6/2011 |

OTHER PUBLICATIONS

International Search Report dated Apr. 28, 2014 issued in PCT/JP2014/052068.
Notice of Allowance dated Jun. 7, 2016 from related Japanese Patent Application No. 2015-508130.
Extended Supplementary European Search Report dated Oct. 24, 2016 in related European Patent Application No. 14 77 2848.9.

_(10,085,618 B2)_

TREATMENT TOOL EXCHANGING DEVICE AND MEDICAL SYSTEM

This application is a continuation claiming priority on the basis of U.S. Patent Application No. 61/806,128 provisionally applied in US on Mar. 28, 2013 and based on PCT/JP2014/052068 filed on Jan. 30, 2014. The contents of both the PCT application and the U.S. Provisional Application are incorporated herein by reference.

TECHNICAL FIELD

The present invention relates to a treatment tool exchanging device and a medical system.

BACKGROUND ART

In the related art, in medical treatment using an endoscope, medical treatment is performed while exchanging a plurality of treatment tools with respect to the endoscope. For example, a medical system including a plurality of treatment tools is disclosed in Japanese Unexamined Patent Application, First Publication No. 2008-188109.

SUMMARY OF INVENTION

According to a first aspect of the present invention, a treatment tool exchanging device is provided that switches and holds a plurality of treatment tools for treating a target to be treated, the treatment tool exchanging device includes: a flexible insertion part in which a plurality of treatment tool channels are formed, wherein the plurality of treatment tools are inserted into the plurality of treatment tool channels and the plurality of treatment tool channels define insertion paths for the treatment tools; a driving part which advances each of the plurality of treatment tools, that are inserted through the treatment tool channels, within the treatment tool channel, and retracts each of the plurality of treatment tools within the treatment tool channel; a manipulating part which manipulates the plurality of treatment tools and treats the target; and a control unit which controls an amount of protrusion from the treatment tool channel of the treatment tool in the state where the treatment tool protrudes from a distal end of the treatment tool channel among the plurality of treatment tools. The insertion part has a switching part that changes the insertion path of the treatment tool to be inserted.

According to a second aspect of the present invention, in the treatment tool exchanging device related to the first aspect, the switching part may include: a communication channel that allow the plurality of treatment tool channels to communicate with each other; and a door that closes at least one of the plurality of treatment tool channels and guides the treatment tool to at least one of the remaining treatment tool channels that are not closed.

According to a third aspect of the present invention, in the treatment tool exchanging device related to the first aspect, the switching part may include: a communication channel that allows the plurality of treatment tool channels to communicate with each other; a door that closes at least one of the plurality of treatment tool channels and guides the treatment tool to at least one of the remaining treatment tool channels that are not closed, and a path length adjusting part that adjusts a path length of the treatment tool channel.

According to a fourth aspect of the present invention, a medical system includes: the treatment tool exchanging device related to the first aspect; a manipulator that actuates the treatment tool exchanging device; and a master input unit that performs manipulation input for giving an instruction on the operation of the treatment tool exchanging device and the manipulator.

DESCRIPTION OF EMBODIMENTS

First Embodiment

Figure 1:
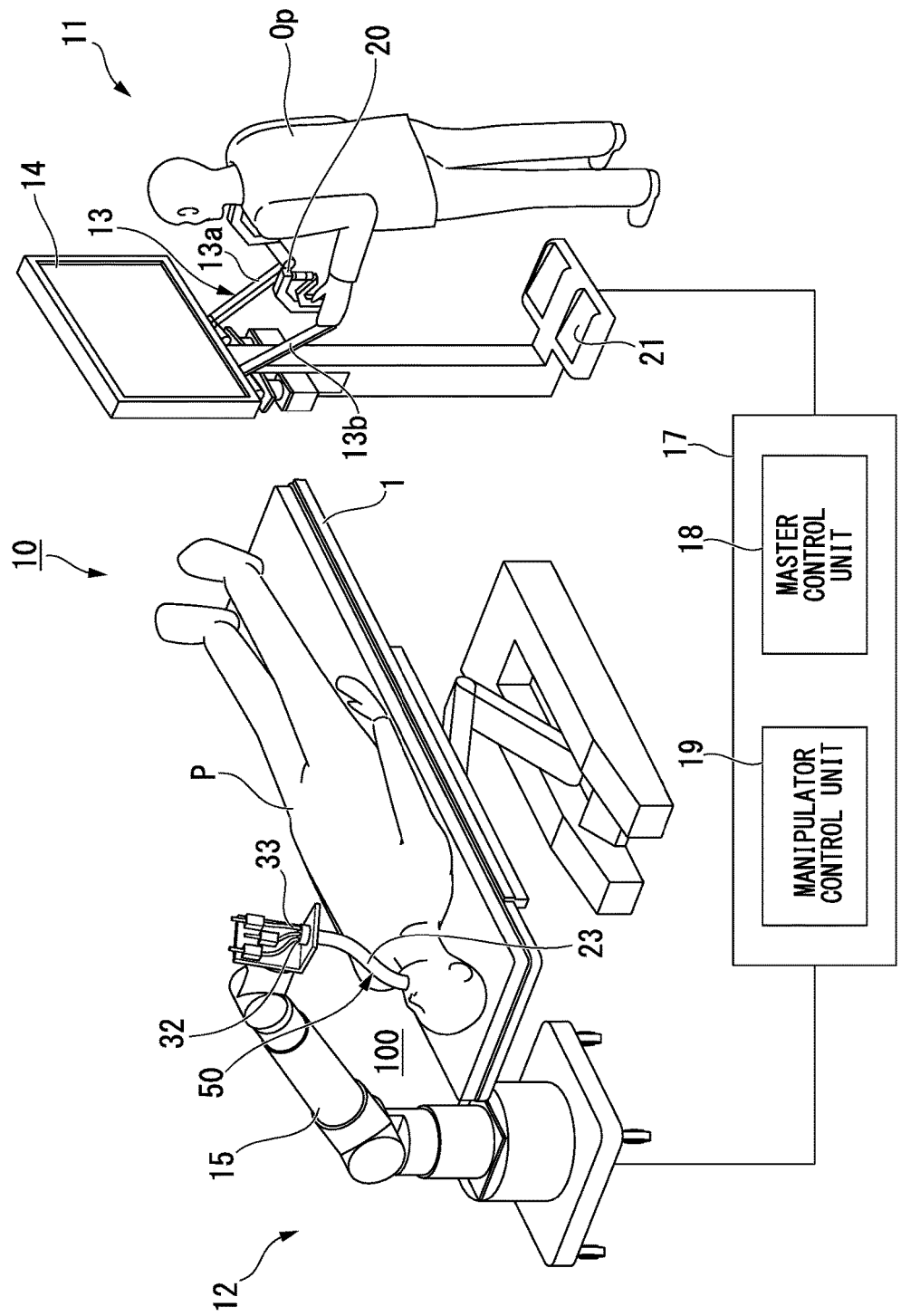
FIG. 1 is an overall view of a medical system of a first embodiment of the present invention.

A first embodiment of a treatment tool exchanging device and a medical system of the present invention will be described. FIG. 1 is an overall view of the medical system having the treatment tool exchanging device of the first embodiment of the present invention.

In the present embodiment, a medical system 10 having a treatment tool exchanging device 100 includes a master input unit 11 and a slave manipulator (manipulator) 12. The master input unit 11 has a plurality of master arms 13 for performing manipulation input, and a display unit 14 that displays an acquired image. The slave manipulator 12 has a slave arm 15.

The treatment tool exchanging device 100 includes an insertion part 16, driving parts 42 and 43, a grasping part (manipulating part) 20, and a control unit 17.

The insertion part 16 has flexibility, and the insertion part 16 is formed with a plurality of treatment tool channels 26 and 27 that define insertion paths for a plurality of treatment tools 29 and 31. The plurality of treatment tools 29 and 31 are inserted into the plurality of treatment tool channels 26 and 27. The driving parts 42 and 43 advance the plurality of treatment tools 29 and 31, which are inserted through the treatment tool channels 26 and 27, within the treatment tool channels 26 and 27, and retract the plurality of treatment tools 29 and 31 within the treatment tool channels 26 and 27. The grasping part 20 manipulates the plurality of treatment tools 29 and 31, and treats a target region. The control unit 17 controls the amounts of protrusion of the treatment tools 29 and 31, which are in the state of protruding from the distal ends of the treatment tool channels 26 and 27 among the plurality of treatment tools 29 and 31, from the treatment tool channels 26 and 27. Additionally, the insertion part 16 has switching parts 105 and 107 that change the insertion paths for the treatment tools 29 and 31 to be inserted.

The insertion part will be described in detail below.

The medical system 10 remotely controls the slave arm 15 and the insertion part 16 so as to follow the manipulation of the master arms 13 by a surgeon (operator) Op. Manipulation commands via the master arms 13 are transmitted to a master control unit 18 of the control unit 17. A conversion processing is appropriately performed to manipulation commands if necessary. After that, the manipulation commands are input to the manipulator control unit 19. Then, the manipulator control unit 19 sends actuating signals to the slave manipulator 12, thereby actuating the slave arm 15 and the insertion part 16.

The master input unit 11 displays an image, which is acquired by an observation member (refer to FIG. 2) 34, on the display unit 14. Each master arm 13 has a well-known configuration in which multiaxial operation is possible, and includes the grasping part 20 as a manipulating part, which is grasped by the surgeon Op and issues a manipulation command, on the distal end side near the surgeon Op.

The master input unit 11 is provided with a foot switch 21 that functions as a mode input unit for selecting and inputting the modes of the insertion part 16. The configuration of the mode input unit is not limited to the foot switch 21 and may be, for example, buttons provided on the grasping part 20, a touch panel displayed on the display unit 14, or the like, and there is no particular limitation in specific configuration. Additionally, these may be appropriately combined.

The slave manipulator 12 is installed on a surgical table 1 on which a patient P is placed or in the vicinity of the surgical table 1. Since the slave arm 15 is configured to have a plurality of multiple degree-of-freedom joints, multiaxial operation is possible. Each multiple degree-of-freedom joint is individually driven by a power unit (not shown). As the power unit, for example, a motor (servo motor) having a servo mechanism including an incremental encoder, a speed reducer, and the like, can be used. The insertion part 16 to be inserted into the body of the patient P is attached to a distal end part of the slave arm 15.

Figure 2:
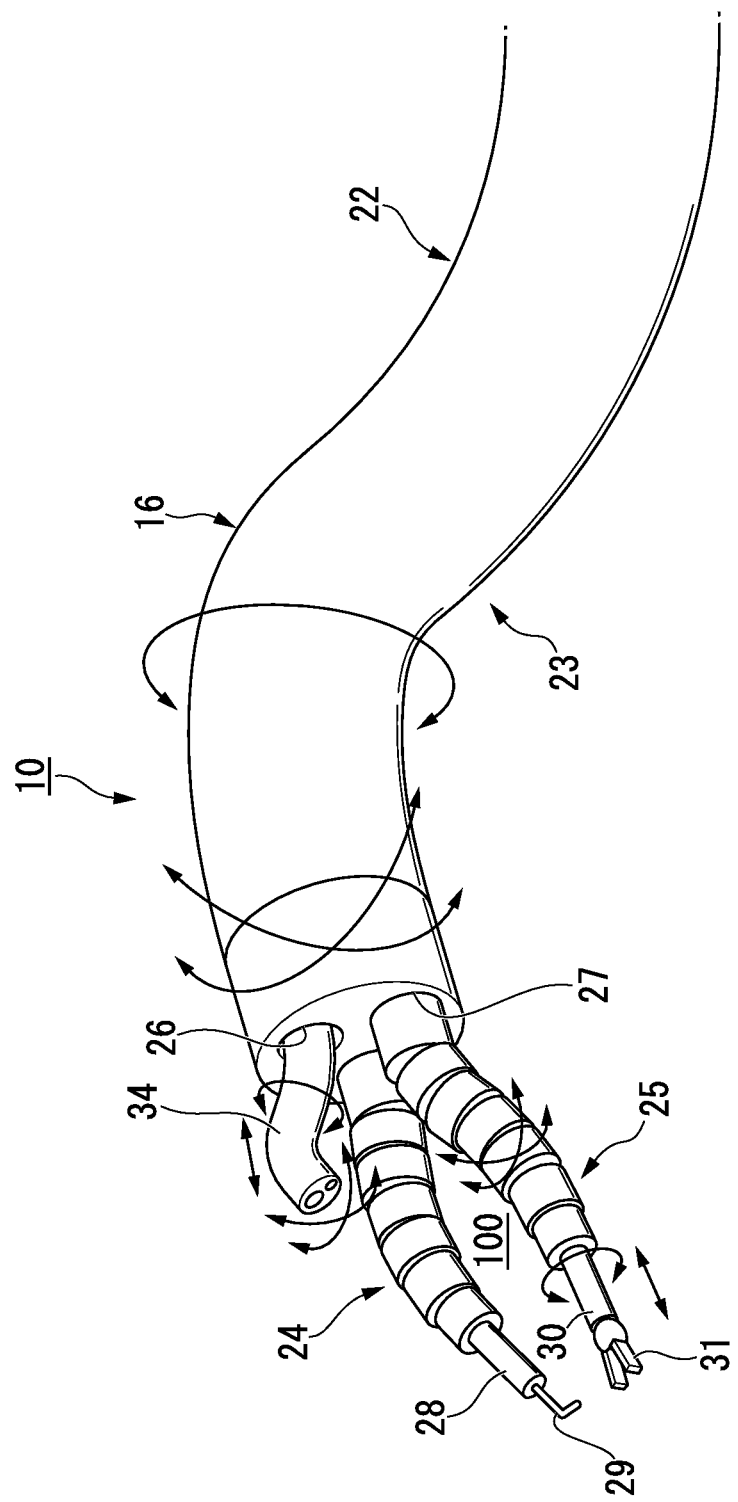
FIG. 2 is an appearance view of an insertion part of the medical system of the first embodiment of the present invention.

Next, the structure of the insertion part 16 of the medical system 10 will be described. FIG. 2 is an appearance view of the insertion part 16 of the medical system 10. As shown in FIG. 2, the insertion part 16 has a flexible part 22, a bending part 23, a right arm 24, and a left arm 25. The flexible part 22 is elongated and has flexibility. The bending part 23 has a well-known structure in which a plurality of joint rings, bending pieces, or the like are arranged. The bending part 23 can be bent in biaxial directions orthogonal to an axis of the insertion part 16 by advancing and retracting a manipulating member (not shown), such as a wire connected to a joint ring or the like closest to the distal end side, with respect to an axial direction of the insertion part 16. The respective arms 24 and 25 are attached to a distal end part of the bending part 23.

The insertion part 16 is attached to the slave arm 15 so as to be rotatable about its own axis. A manipulating member (not shown) that rotates the insertion part 16 and a manipulating member for manipulating the bending part 23 are pulled out from a base end side of the insertion part 16, and are fixed to pulleys (not shown) or the like, respectively. Shafts of the respective pulleys are respectively coupled to driving shafts (not shown) provided in the slave arm 15. Each driving shaft is provided with a driving mechanism (not shown) that has the same configuration as the above-described power unit, and the bending manipulation and rotational manipulation of the bending part 23 can be performed by rotating the driving shafts with the driving mechanisms. In the present specification, a floor surface side of the slave arm 15 in the slave manipulator 12 is referred to as a proximal end side, a proximal end part, and a proximal end, and a side distant from the floor surface is referred to as a distal end side, a distal end part, and a distal end.

The respective arms 24 and 25 are attached to the distal end of the bending part 23. The respective arms 24 and 25 have the same bending structure as the bending part 23, and can be bent in biaxial directions orthogonal to the axes of the respective arms 24 and 25. Additionally, the respective arms 24 and 25 are formed in a tubular shape having an inner cavity. The inner cavity of the right arm 24 communicates with an inner cavity of the right treatment tool channel 26 provided in the insertion part 16. The inner cavity of the left arm 25 communicates with an inner cavity of the left treatment tool channel 27 provided in the insertion part 16.

Arm manipulating members for bendingly manipulating the respective arms 24 and 25 have the same aspect as the manipulating member of the bending part 23, and are coupled to arm driving shafts provided in the slave arm 15. The arm manipulating members can bend the respective arms 24 and 25 with arm driving mechanisms.

An elongated sheath part 28 having flexibility for performing treatment, and the right treatment tool 29 provided at a distal end part of the sheath part 28 are inserted through the right treatment tool channel 26 of the right arm 24. Similarly, an elongated sheath part 30 having flexibility for performing treatment, and the right treatment tool 31 provided at a distal end part of the sheath part 30 are inserted through the left treatment tool channel 27 of the left arm 25.

In the medical system 10, a pair of different treatment tools corresponding to various procedures, such as a high-frequency knife, a snare loop, and grasping forceps, are prepared, as the respective treatment tools 29 and 31, and are used by being appropriately exchanged depending on procedures or the like. The respective treatment tools 29 and 31 are inserted into the respective treatment tool channels 26 and 27 of the insertion part 16 from the right treatment tool port (refer to FIG. 1) 32 and the left treatment tool port (refer to FIG. 1) 33 that are provided at a proximal end part of the insertion part 16 on the slave arm 15 side. The respective treatment tools 29 and 31 protrude from distal end openings of the respective arms 24 and 25 through the treatment tool channels 26 and 27 and the respective arms 24 and 25.

Treatment tool manipulating members (not shown), such as wires, are attached to the respective treatment tools 29 and 31. The treatment tool manipulating members are advanced and retracted with respect to the respective sheath parts 28 and 30, thereby driving the respective treatment tools 29 and 30. The treatment tool manipulating members are coupled to treatment tool driving shafts provided in the slave arm 15 in the same aspect as the manipulating member of the bending part 23 and the arm manipulating members, and can drive the respective treatment tools 29 and 31 with the treatment tool driving mechanisms.

Additionally, the respective treatment tools 29 and 31 are capable of advancing, retracting, and rotating with the respective arms 24 and 25 and the bending part 23. The protrusion lengths of the respective treatment tools 29 and 31 from the distal end openings of the respective arms 24 and 25 can be adjusted by advancing and retracting the respective treatment tools 29 and 31. The respective treatment tools 29 and 31 can be adjusted to a suitable state with respect to a procedure by rotating the respective treatment tools 29 and 31. Manipulating members for advancing, retracting, and rotating the treatment tools 29 and 31, similar to the above-described respective manipulating members, are also connected to the driving shafts and the driving mechanisms that are provided at the slave arm 15, respectively.

An observation member 34 that acquires an image in front of the insertion part 16 protrudes from the distal end of the insertion part 16, in addition to the respective arms 24 and 25. The observation member 34 is inserted through an observation member channel (not shown) provided in the insertion part 16, and is capable of advancing, retracting, and rotating with respect to the insertion part 16. The observation member 34 has a bending part 35 on a distal end side thereof, and is bendable. As such an observation member 34, various well-known endoscopes or the like can be suitably used. Since a manipulating member for performing various kinds of manipulation of the observation member 34 is also coupled to the slave arm 15 similar to the insertion part 16, the manipulating member can be manipulated via the master input unit 11.

Figure 3:
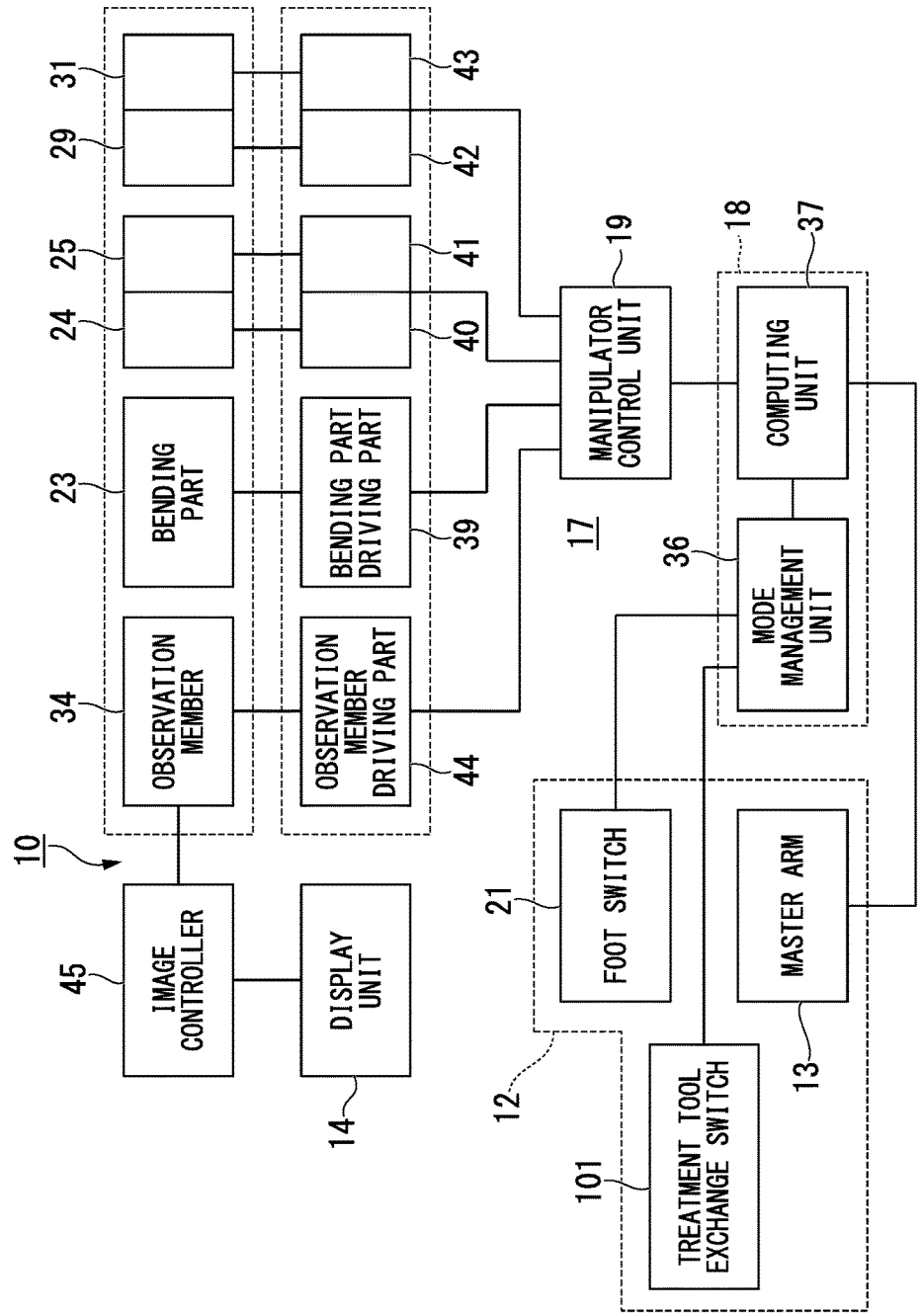
FIG. 3 is a block diagram of the medical system.

Next, the block configuration of the medical system 10 will be described. FIG. 3 is a block diagram of the medical system 10. As shown in FIG. 3, the master control unit 18 includes a mode management unit 36 connected to the foot switch 21, and a computing unit (control unit) 37 connected to the master arms 13 and the mode management unit 36. A manipulation input regarding a mode of the insertion part 16 using the foot switch 21 is sent to the mode management unit 36, and a signal indicating the selected mode is sent from the mode management unit 36 to the computing unit 37. The computing unit 37 generates signals for actuating respective parts of the slave manipulator 12 on the basis of the manipulation input from the master arms 13 and the signal received from the mode management unit 36, sends the signals to the manipulator control unit 19, and controls the operation of respective parts of the insertion part 16.

The manipulator control unit 19 is connected to a bending part driving part 39 that drives the bending part 23, a right arm driving part 40 that drives the right arm 24, and a left arm driving part 41 that drives the left arm 25. The manipulator control unit 19 is connected to the right treatment tool driving part 42 that drives the right treatment tool 29, the left treatment tool driving part 43 that drives the left treatment tool 31, and an observation member driving part 44 that drives the observation member 34. Detection means, such as encoders, which detect the amounts of displacement of the manipulating members of the coupled respective parts, are attached to driving shafts of the respective driving parts 39, 40, 41, 42, 43, and 44. Signals indicating the amounts of displacement are sent to the manipulator control unit 19 from the respective driving parts, and various amounts of manipulation, such as the amounts of bending and protrusion of the respective parts, are recognized. The manipulator control unit 19 generates driving signals on the basis of the amounts of manipulation and the signals received from the computing unit 37, and sends the driving signals to the respective driving parts. Accordingly, the insertion part 16 and the respective parts inserted through the insertion part 16 are operated.

The observation member 34 is connected to an image controller 45. The image in a surgical field acquired by the observation member 34 is sent to the display unit 14 via the image controller 45, and the image is displayed in the display unit 14.

The medical system 10 has a treatment tool exchange switch 101 that constitutes a portion of the treatment tool exchanging device 100. The treatment tool exchange switch 101 is connected to the mode management unit 36. It is preferable that the treatment tool exchange switch 101 is provided at a position where a hand of the surgeon Op may easily reach the switch.

Figure 4:
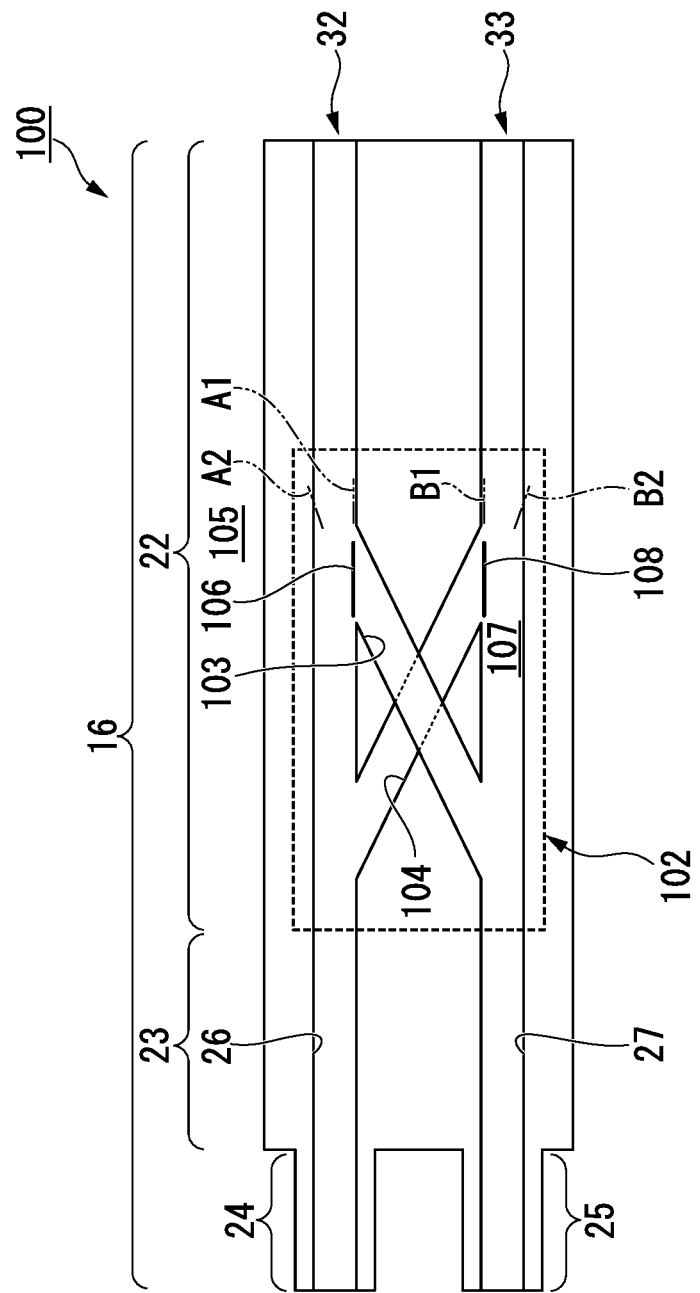
FIG. 4 is a sectional schematic view of the insertion part in a treatment tool exchanging device of the first embodiment of the present invention.
Figure 5:
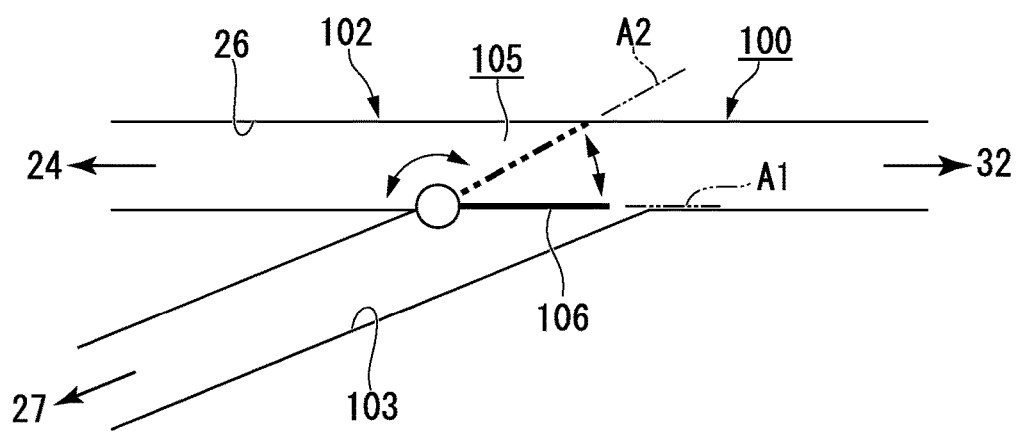
FIG. 5 is an enlarged sectional view of main parts of the insertion part of the treatment tool exchanging device.

Next, the specific structure of the treatment tool exchanging device 100 will be described. FIG. 4 is a sectional schematic view of the insertion part 16 in the treatment tool exchanging device 100. FIG. 5 is an enlarged sectional view of main parts of the insertion part 16 of the treatment tool exchanging device 100. As shown in FIG. 4, the treatment tool exchanging device 100 has a treatment tool exchange part 102 in the flexible part 22 in the vicinity of a proximal end of the bending part 23 in the insertion part 16.

In the treatment tool exchange part 102, the right treatment tool channel 26 divides into two branches. One branched channel communicates with the right arm 24. The other branched channel is joined to and connected to communicate with the left treatment tool channel 27 through a first communication channel 103 bent at an acute angle with respect to an axis direction that faces the right arm 24 of the right treatment tool channel 26. Similarly, the left treatment tool channel 27 is branched into two, and one branched channel communicates with the left arm 25. The other branched channel is joined to and connected to communicate with the right treatment tool channel 26 through a second communication channel 104 bent at an acute angle with respect to an axis direction that faces the left arm 25 of the left treatment tool channel 27.

The treatment tool exchanging device 100 has a first switching part (switching part) 105 at the portion of the right treatment tool channel 26 connected to the first communication channel 103. The first switching part 105 has a first door (door) 106. Similarly, the treatment tool exchanging device 100 has a second switching part 107 at the portion of the left treatment tool channel 27 connected to the second communication channel 104. The second switching part (switching part) 107 has a second door (door) 108.

The first door 106 closes the right treatment tool channel 26 of the right treatment tool channel 26 and the left treatment tool channel 27, to guide the treatment tools 29 and 31 to the left treatment tool channel 27 that is not closed.

The second door 108 closes the left treatment tool channel 27 of the left treatment tool channel 26 and the left treatment tool channel 27, to guide the treatment tools 29 and 31 to the right treatment tool channel 28 that is not closed.

As shown in FIG. 5, the treatment tool exchanging device 100 can switch the first door 106 to a first position A1 and a second position A2. When the first door 106 is located at the first position A1, the right treatment tool port 32 is blocked from the inside of the left arm 25, and the right treatment tool port 32 is connected to communicate with the inside of the right arm 24. When the first door 106 is located at the second position A2 unlike this, the right treatment tool port 32 is blocked from the inside of the right arm 24, and the right treatment tool port 32 is connected to communicate with the inside of the left arm 25 through the first communication channel 103.

As shown in FIG. 4, the treatment tool exchanging device 100 can switch the second door 108 to a first position B1 and a second position B2. When the second door 108 is located at the first position B1, the left treatment tool port 33 is blocked from the inside of the right arm 24, and the left treatment tool port 33 is connected to communicate with the inside of the left arm 25. When the second door 107 is located at the second position B2 unlike this, the left treatment tool port 33 is blocked from the inside of the left arm 25, and the left treatment tool port 33 is connected to communicate with the inside the right arm 24 through the second communication channel 104.

In this way, the treatment tool exchanging device 100 can select whether the right treatment tool 29 inserted from the right treatment tool port 32 is inserted through the right arm 24 or is inserted through the left arm 25 by switching between left and right. Similarly, the treatment tool exchanging device 100 can select whether the left treatment tool 31 inserted from the left treatment tool port 33 is inserted through the left arm 25 or is inserted through the right arm 24 by switching between left and right.

The respective doors 106 and 108 of the respective switching mechanisms 105 and 107 are controlled by manipulating members, such as wires (not shown). The wires for controlling the respective doors 106 and 108 are connected to, for example, the bending part driving part 39. Additionally, the positions of the respective doors 106 and 108 may be detected by performing calculation from information from sensors that measure the displacements of manipulating members, such as encoders in the driving parts, or photosensors (not shown) may detect the positions of the respective doors 106 and 108.

Additionally, although the respective switching mechanisms 105 and 107 are present only at the branched parts of the respective treatment tool channels 26 and 27, the switching mechanisms may be located at both branched parts and joined parts. In that case, the respective treatment tools 29 and 31 can be prevented from returning to the respective treatment tool port 33 and 32 sides at the joined parts.

Figure 6:
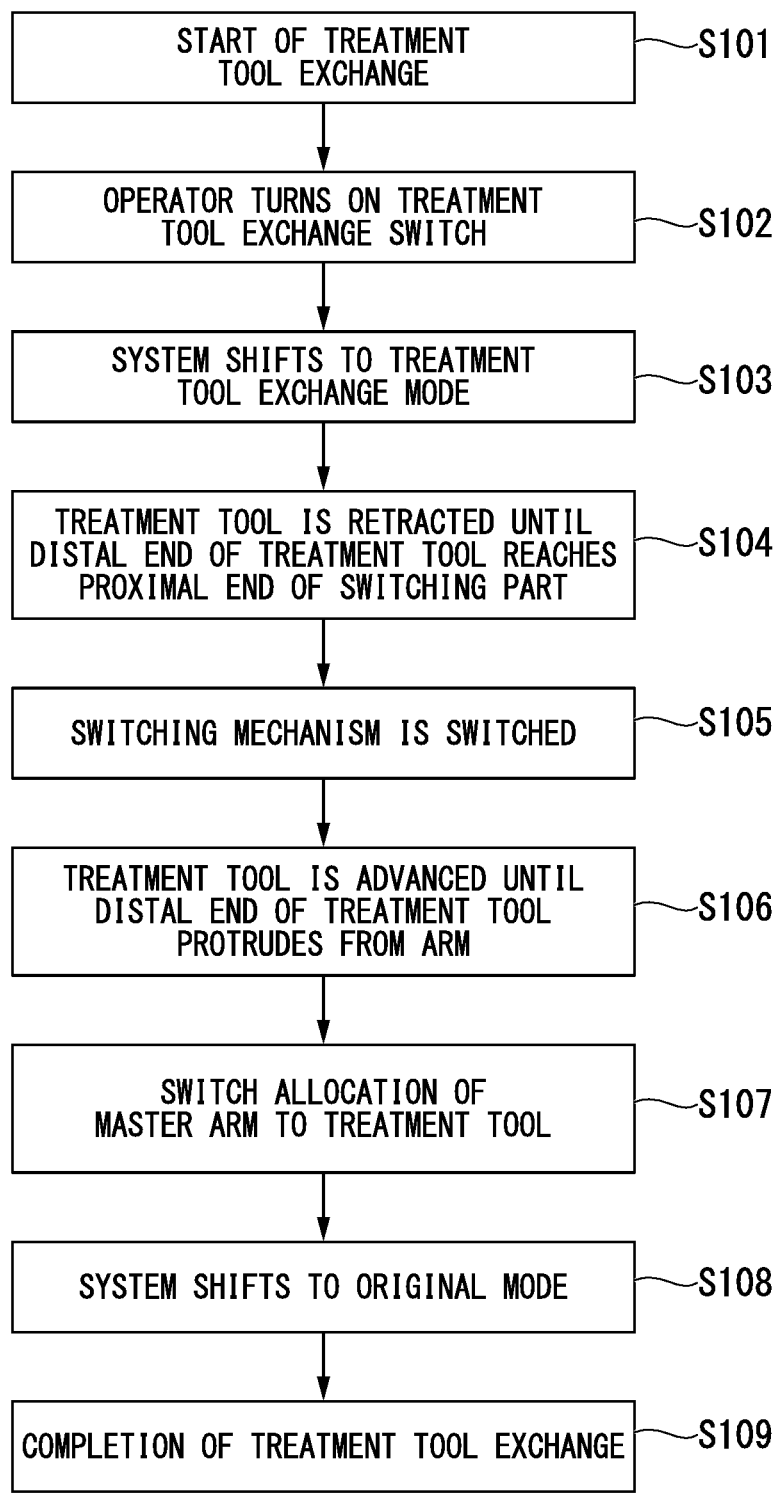
FIG. 6 is a flowchart for describing a process for treatment tool exchange in the treatment tool exchanging device.
Figure 7:
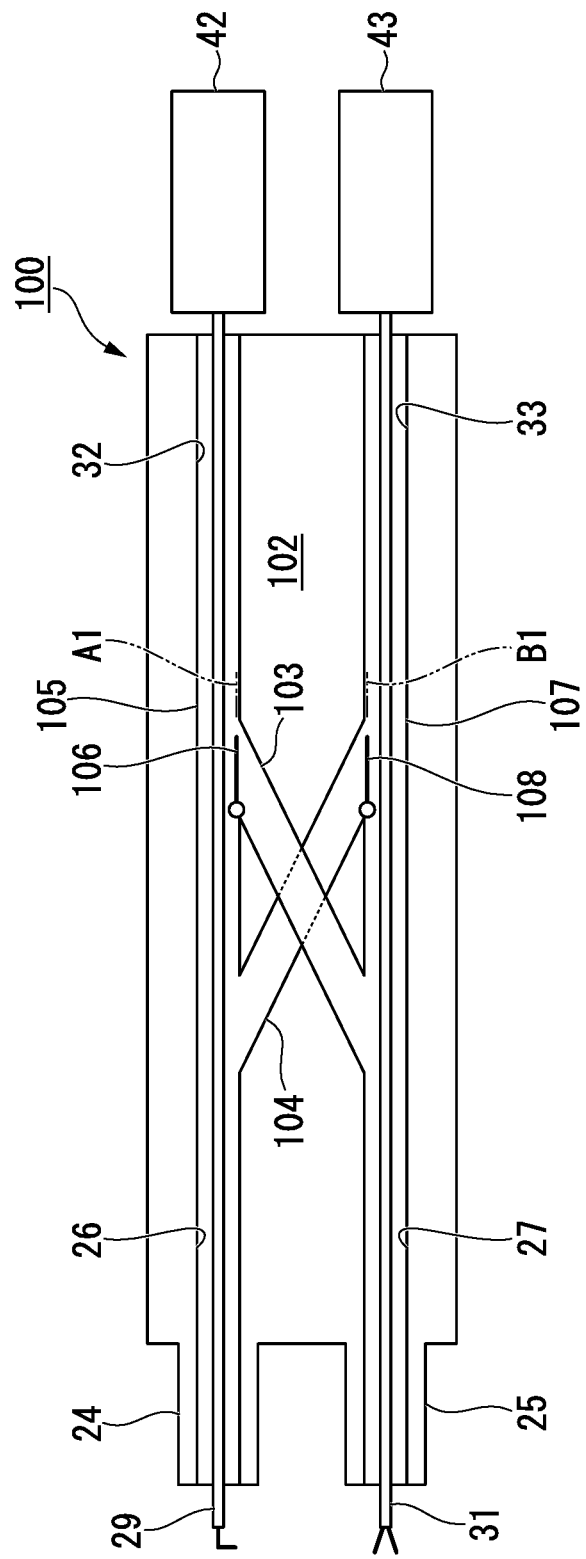
FIG. 7 is a sectional schematic view showing a first step in the treatment tool exchange of the treatment tool exchanging device.
Figure 8:
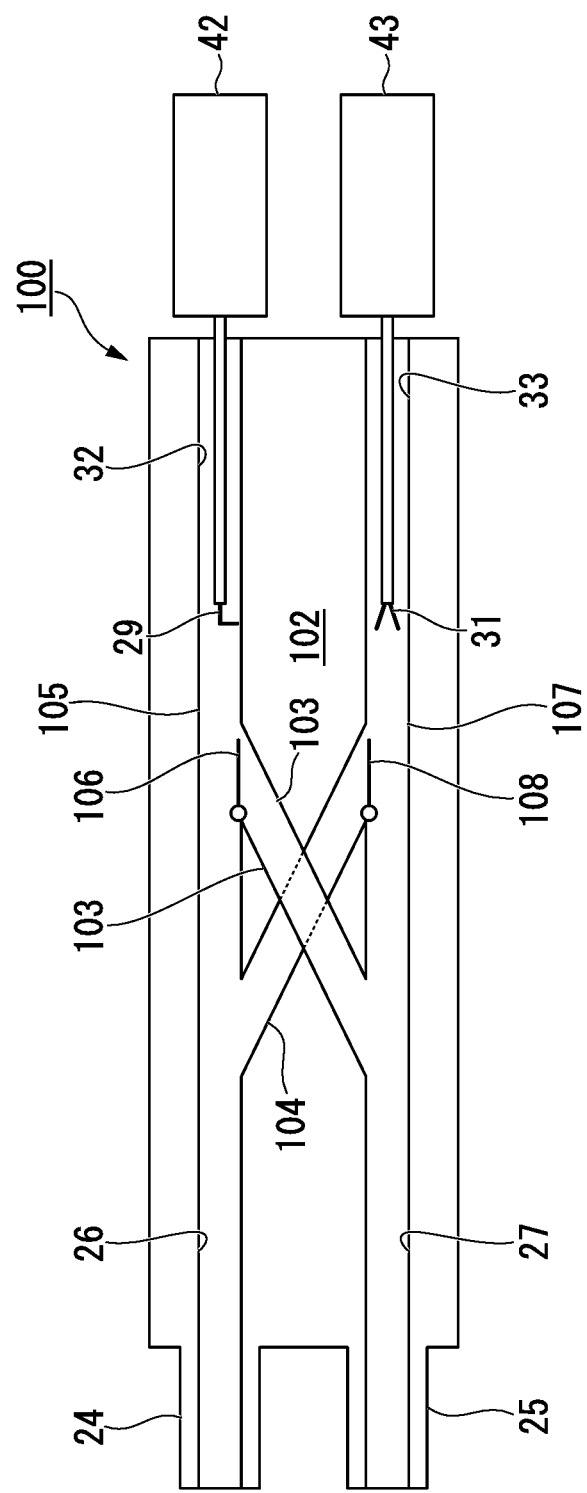
FIG. 8 is a sectional schematic view showing a second step in the treatment tool exchange of the treatment tool exchanging device.
Figure 9:
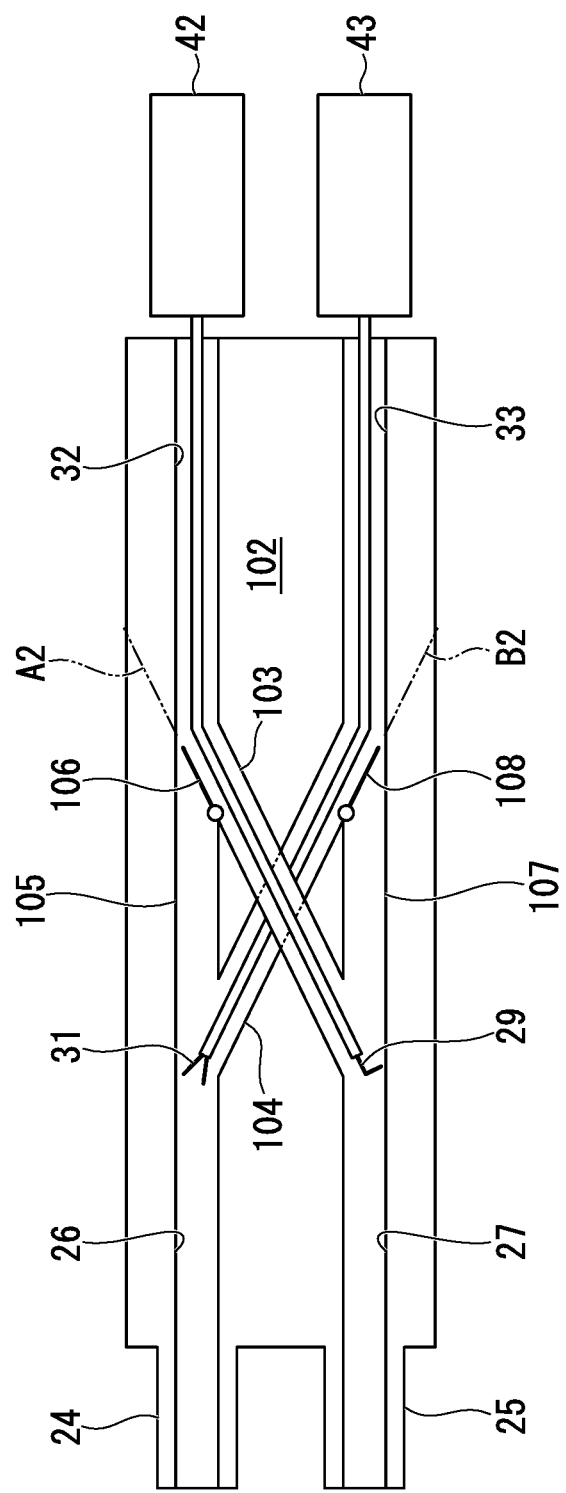
FIG. 9 is a sectional schematic view showing a third step in the treatment tool exchange of the treatment tool exchanging device.
Figure 10:
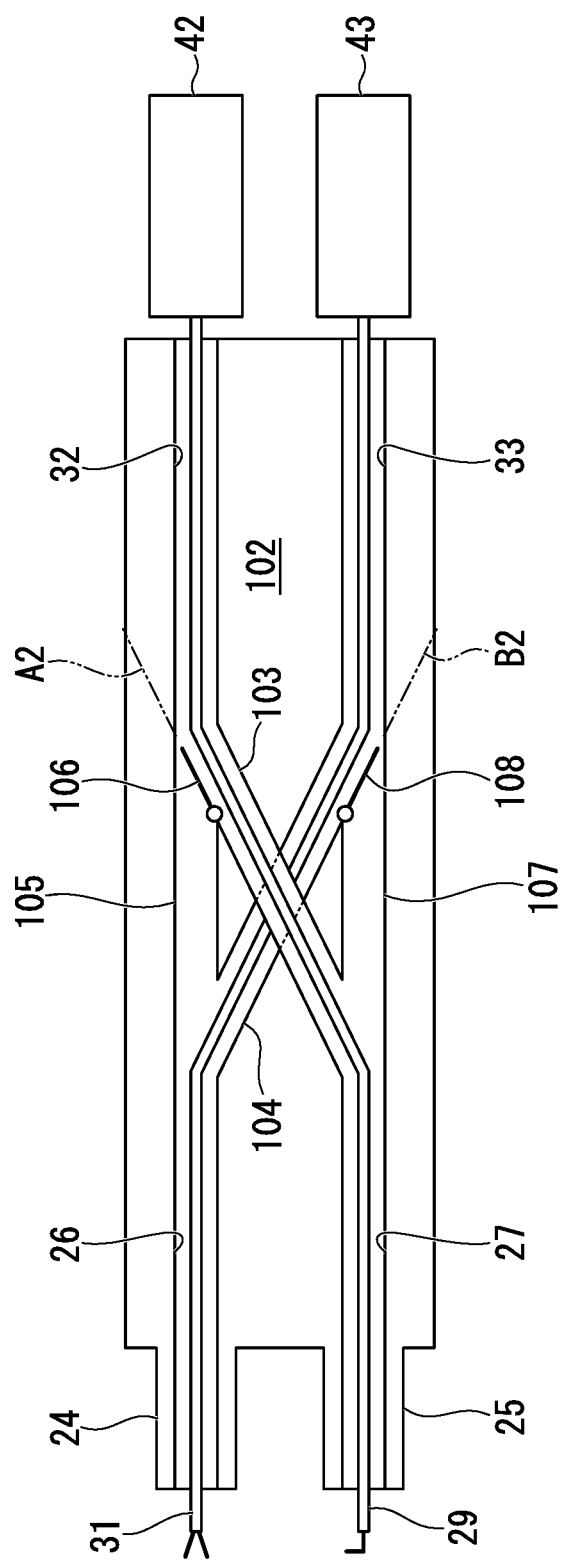
FIG. 10 is a sectional schematic view showing a fourth step in the treatment tool exchange of the treatment tool exchanging device.

Next, a procedure performed by the medical system 10 and the specific operation of the treatment tool exchanging device 100 will be described. FIG. 6 is a flowchart for describing a process for treatment tool exchange in the treatment tool exchanging device 100. FIG. 7 is a sectional schematic view showing a first step in the treatment tool exchange of the treatment tool exchanging device 100. FIG. 8 is a sectional schematic view showing a second step in the treatment tool exchange of the treatment tool exchanging device 100. FIG. 9 is a sectional schematic view showing a third step in the treatment tool exchange of the treatment tool exchanging device 100. FIG. 10 is a sectional schematic view showing a fourth step in the treatment tool exchange of the treatment tool exchanging device 100.

As shown in FIG. 1, the surgeon Op first inserts the insertion part 16 into the body from a natural opening of the patient P. Although an example in which the insertion part is inserted from a mouth is shown herein, the insertion part 16 may be inserted from other natural openings, such as the anus, instead of the mouth. The surgeon Op moves the distal end of the insertion part 16 to the target region of a procedure, while checking the image of the observation member 34 with the display unit 14.

Next, the surgeon Op selects the respective treatment tools 29 and 31 in accordance with a procedure to be performed, mounts the selected respective treatment tools 29 and 31 on the slave arm 15 so as to be inserted into the respective treatment tool ports 32 and 33 of the insertion part 16, and causes the respective treatment tools 29 and 31 to protrude from the respective arms 24 and 25. The amounts of protrusion in this case may be predetermined amounts of initial protrusion that are set in advance, for example, may be the maximum amounts of protrusion beyond which the respective treatment tools 29 and 31 cannot protrude any more or may be the minimum amounts of protrusion from the respective arms 24 and 25. Thereafter, the surgeon Op manipulates the respective arms 24 and 25 while viewing the image from the observation member 34, and performs a desired procedure on a target region.

In this case, if necessary, the respective left and right treatment tools 29 and 31 may be exchanged with others, or the distal end part of the insertion part 16 may be moved to other target regions so as to perform a procedure.

Then, as shown in FIG. 6, in Step S101, exchange control of the respective treatment tools 29 and 31 starts. Step S102 is performed after Step S101. In Step S102, the operator Op pushes the treatment tool exchange switch 101. Step S103 is performed after Step S102. In Step S103, a treatment tool exchange mode is set by detecting that the treatment tool exchange switch 101 has been pushed by the mode management unit 36. Step S104 is performed after Step S103.

In this case, as shown in FIG. 7, the right treatment tool 29 is inserted through the right arm 24 from the right treatment part port 32, and the left treatment tool 31 is inserted through the left arm 25 from the left treatment tool port 33. The first door 106 is located at the first position A1, and the second door 108 is located at the first position B1.

In Step S104, the respective treatment tool driving parts 42 and 43 are driven such that the distal ends of the respective treatment tools 29 and 31 are retracted to a proximal end of the treatment tool exchange part 102. Step S105 is performed after Step S104.

As shown in FIG. 8, the distal ends of the respective treatment tools 29 and 31 are retracted to the proximal end of the treatment tool exchange part 102 by the driving of the respective treatment tool driving parts 42 and 43.

In Step S105, the first switching part 105 and the second switching part 107 are driven. Step S106 is performed after Step S105. The first door 106 is switched from the first position A1 to the second position A2 by the driving of the first switching part 105. Simultaneously, the second door 108 is switched from the first position B1 to the second position B2 by the driving of the second switching part 107.

In Step S106, the respective treatment tool driving parts 42 and 43 are driven for return until the distal ends of the respective treatment tools 29 and 31 protrude from the distal ends of the respective arms 24 and 25 (the treatment tools 29 and 31 are advanced). Step S107 is performed after Step S106.

As shown in FIG. 9, the right treatment tool 29 of which the distal end has been retracted to the proximal end of the treatment tool exchange part 102 is inserted through the first communication channel 103 via the first door 106 located at the second position A2. Simultaneously, the left treatment tool 31 of which the distal end has been retracted to the proximal end of the treatment tool exchange part 102 is inserted through the second communication channel 104 via the second door 108 located at the second position B2.

As shown in FIG. 10, the right treatment tool 29 inserted through the first communication channel 103 protrudes from the left arm 25 after being inserted through the left arm 25. Simultaneously, the right treatment tool 31 inserted through the second communication channel 104 protrudes from the right arm 24 after being inserted through the right arm 24. Here, it is confirmed on the basis of the movement of the respective doors 106 and 108 of the respective switching parts 105 and 107 that the respective treatment tools 29 and 31 have been exchanged with others.

In this case, the path length from a proximal end part of the right treatment tool channel 26 to the left arm 25 is different from the path length from a proximal end part of the right treatment tool channel 26 to the right arm 24. Specifically, the path from the proximal end part of the right treatment tool channel 26 to the left arm 25 is longer than the path from the proximal end part of the right treatment tool channel 26 to the right arm 24 by the path length of the first communication channel 103. The amounts of protrusion to the respective arms 24 and 25 from the distal ends of the respective treatment tools 29 and 31 are determined in advance from the lengths of the respective treatment tools 29 and 31 and the lengths of the respective treatment tool channels 26 and 27. Therefore, after the exchange of the respective treatment tools 29 and 31, increases in the path lengths are computed by the computing unit 37, and the amounts of advance of the respective treatment tools 29 and 31 are increased according to the increases in the path lengths such that the respective treatment tools 29 and 31 protrude from the distal ends of the respective arms 24 and 25 with the same amount of protrusion.

In Step S107, allocation to the respective treatment tools 29 and 31 of the master arms 13 is switched. Step S108 is performed after Step S107.

Here, before the exchange of the respective treatment tools 29 and 31, a master arm 13 is allocated such that the right treatment tool driving part 42 of the right treatment tool 29 is driven by the right arm 13a. However, after the exchange of the respective treatment tools 29 and 31, allocation is made such that the treatment tool driving part 43 of the treatment tool 31 is driven by the right arm 13a. Similarly, before the exchange of the respective treatment tools 29 and 31, a master arm 13 is allocated such that the left treatment tool driving part 43 of the left treatment tool 31 is driven by the left arm 13b. However, after the exchange of the respective treatment tools 29 and 31, a master arm is allocated such that the treatment tool driving part 42 of the treatment tool 29 is driven by the left arm 13b.

In Step S108, the treatment tool exchange mode is shifted to an original normal mode by the mode management unit 36. Step S109 is performed after Step S108.

The treatment tool exchange is completed in Step S109.

If all procedures are finished, the surgeon Op extracts the insertion part 16 from the patient P, and ends a series of operations.

Here, when exchange of the respective treatment tools 29 and 31 is performed again, the exchange can be performed using the flowchart shown in FIG. 6. In this case, the positions of the respective doors 106 and 108 of the respective switching parts 105 and 107 are moved to positions different from those before the exchange.

In the present embodiment, it is confirmed on the basis of the movement of the respective doors 106 and 108 of the respective switching parts 105 and 107 that the respective treatment tools 29 and 31 have been exchanged with others. However, for example, treatment tool presence/absence sensors may be arranged in the respective treatment tool channels 26 and 27. Also, whether the respective treatment tools 29 and 31 are inserted through the respective correct treatment tool channels 26 and 27 may be detected. In this case, if the respective treatment tools 28 and 31 can be detected, proximity sensors, light transmission sensors, or the like can be used as the treatment tool presence/absence sensors.

In the present embodiment, the respective treatment tools 29 and 31 can be exchanged with others simply by driving the respective switching parts 105 and 107 and then advancing the respective treatment tools 29 and 31 after the respective treatment tools 29 and 31 are slightly retracted. That is, it is not necessary to completely extract the respective treatment tools 29 and 31 from the respective treatment tool channels 26 and 27. Therefore, the time taken when the respective treatment tools 29 and 31 are exchanged with others can be markedly shortened.

Additionally, in the present embodiment, the respective switching parts 105 and 107 have the simple structure of the respective doors 106 and 108 and the respective communication channels 103 and 104. Therefore, switching of the treatment tools can be performed without greatly changing existing devices.

Modification Example

Next, a modification example of the above-described first embodiment will be described.

In the present modification example, with respect to a treatment tool or the like of which the distal end structure is unsymmetrical, for example, like the treatment tool 29 including a hook-shaped electrode, there is provided a step of rotating the treatment tool within a treatment tool channel with the exchange of the treatment tool such that the exchange of the treatment tool is appropriately performed.

Specifically, as shown in FIG. 6, the treatment tool 29 is rotated by 180 degrees by the treatment tool driving part 42 that rotates the treatment tool 29 between Step S106 and Step S107.

Accordingly, the treatment tool 29 arranged at the right arm 24 in a state where the distal end thereof faces the left arm 25, for example, as shown in FIG. 7, is arranged at the left arm 25 in a state where the distal end thereof faces the right arm 24 as shown in FIG. 10, between Step S106 and Step S107. Accordingly, a state where a distal end portion of the treatment tool 29 is appropriately directed to a treatment target is maintained. As a result, the treatment after the exchange can be smoothly started when the exchange between the insertion paths of the treatment tool 29 is performed between the right arm 24 and the left arm 25.

With respect to the treatment tool of which the distal end structure is unsymmetrical, means that is installed in the treatment tools and the driving parts to recognize the type of the treatment tools (not shown) may be used so as to rotate only the treatment tool of which the distal end structure is unsymmetrical after the exchange of a treatment tool or so as to rotate all the treatment tools after the exchange without recognizing the distal end structure.

Second Embodiment

Figure 11:
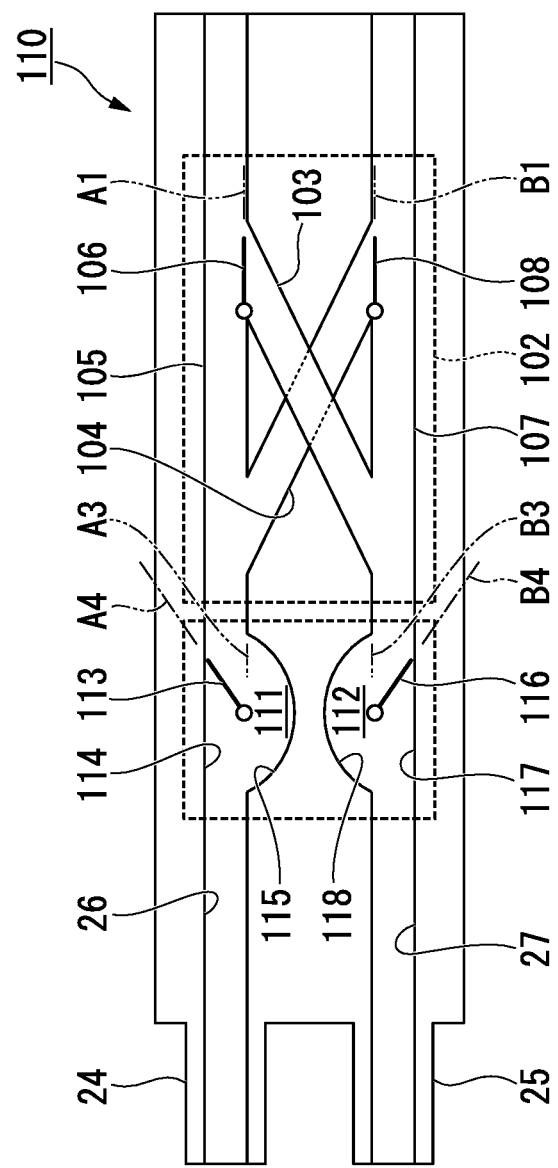
FIG. 11 is a sectional schematic view of the insertion part in a treatment tool exchanging device of a second embodiment of the present invention.

Next, a second embodiment of a treatment tool exchanging device and a medical system of the present invention will be described. FIG. 11 is a sectional schematic view of the insertion part of the treatment tool exchanging device of the second embodiment of the present invention.

In the first embodiment, deviations in the path lengths are dealt with through mechanical switching instead of the changes in the path lengths after the treatment tool exchange being dealt with through the changes in the amounts of advance and retraction by the respective treatment tool driving parts in the present embodiment.

As shown in FIG. 11, a first path length adjusting part 111 and a second path length adjusting part 112 are provided closer to the distal end side than the treatment tool exchange part 102 in the treatment tool exchanging device 110. The first path length adjusting part 111 has a third door 113 that rotates, and when the third door 113 is located at a first position A3, a short channel 114 is set at the right treatment tool channel 26. When the third door 113 is located at the second position A4, a long channel 115 is set at the right treatment tool channel 26. Similarly, the second path length adjusting part 112 has a fourth door 116 that rotates, and when the fourth door 116 is located at a first position B3, a short channel 117 is set at the left treatment tool channel 27. When the fourth door 116 is located at a second position B4, a long channel 118 is set at the left treatment tool channel 27.

Figure 12:
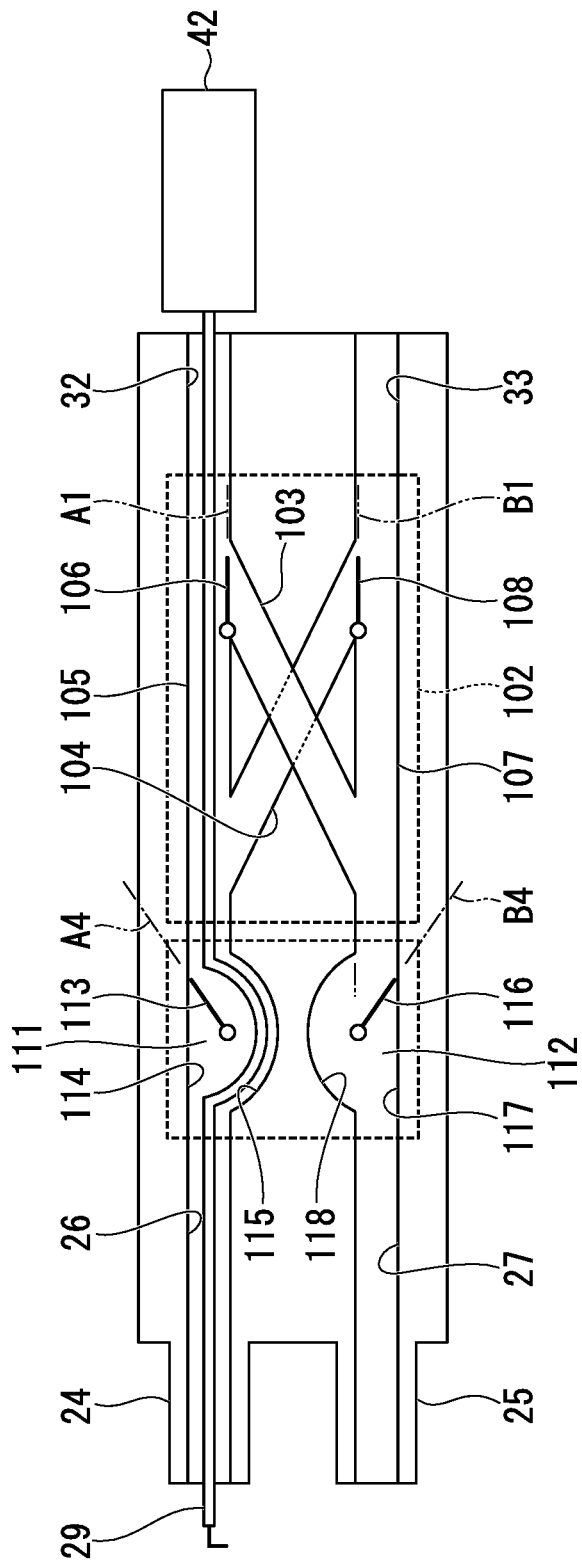
FIG. 12 is a sectional schematic view showing a process in treatment tool exchange of the treatment tool exchanging device.
Figure 13:
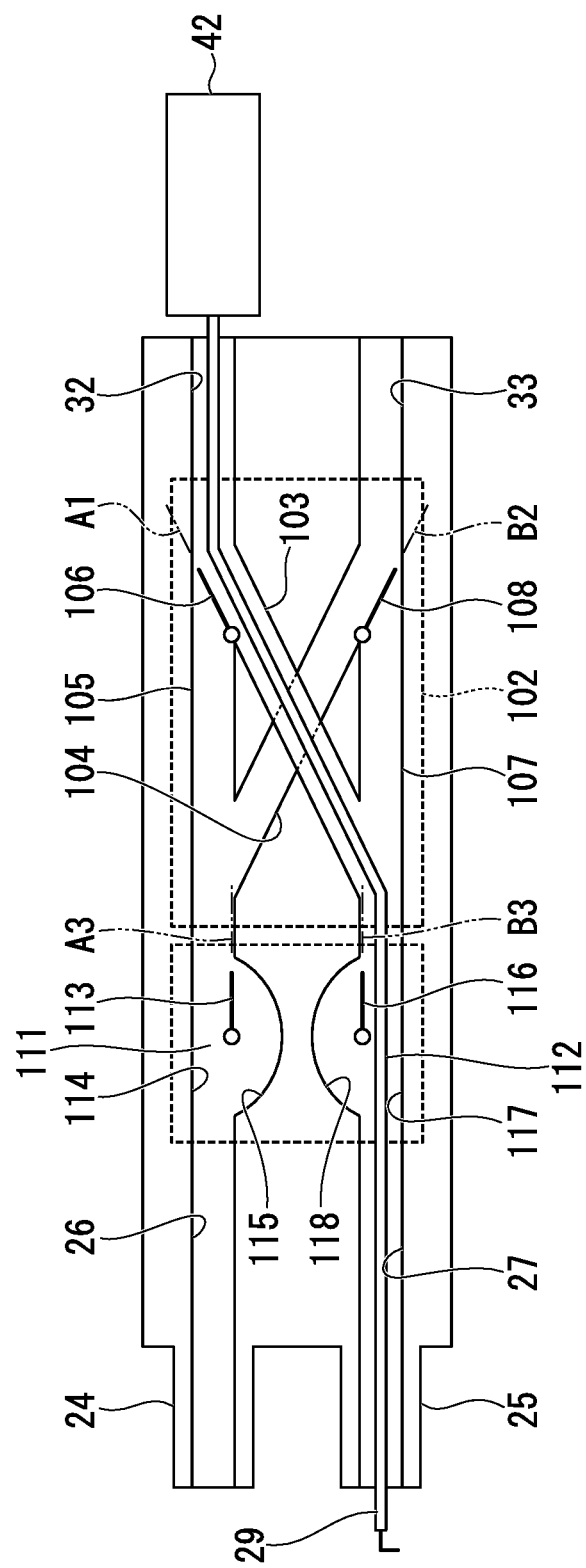
FIG. 13 is a sectional schematic view showing the process in the treatment tool exchange of the treatment tool exchanging device.

Next, the operation of the treatment tool exchanging device 110 will be described. FIG. 12 is a sectional schematic view of a process of the insertion part 16 in the treatment tool exchanging device 110. FIG. 13 is a sectional schematic view of a process of the insertion part 16 in the treatment tool exchanging device 110.

As shown in FIG. 12, as the first door 106 of the treatment tool exchange part 102 is located at the first position A1 and the third door 113 of the first path length adjusting part 111 is located at the second position A4, the long channel 115 is set at the right treatment tool channel 26. Therefore, the right treatment tool 29 is inserted through the right arm 24 through the long channel 115 in the first path length adjusting part 111 after being guided to the first path length adjusting part 111 by the first door 106 of the treatment tool exchange part 102.

As shown in FIG. 13, as the first door 106 of the treatment tool exchange part 102 is located at the second position A2 and the fourth door 116 of the second path length adjusting part 112 is located at the first position A3, the short channel 117 is set at the left treatment tool channel 27. Therefore, the right treatment tool 29 is inserted through the left arm 25 through the short channel 117 in the second path length adjusting part 112 after being guided to the second path length adjusting part 112 via the first communication channel 103 by the first door 106 of the treatment tool exchange part 102.

In this way, since the path lengths of the respective path length adjusting parts 111 and 112 cancel out differences between the path lengths in the treatment tool exchange part 102, the path lengths of the respective treatment tool channels 26 and 27 become substantially the same even after the respective treatment tools 29 and 31 are exchanged with others.

In the present embodiment, even when the path lengths have changed, the amounts of protrusion of the respective treatment tools 29 and 31 from the respective arms 24 and 25 can be arranged through advance/retraction driving by the same amounts of displacement as those before the path lengths of the respective treatment tool driving parts 42 and 43 changed. Therefore, the difference between the path lengths can be reliably eliminated by reliable mechanical switching.

Third Embodiment

Figure 14:
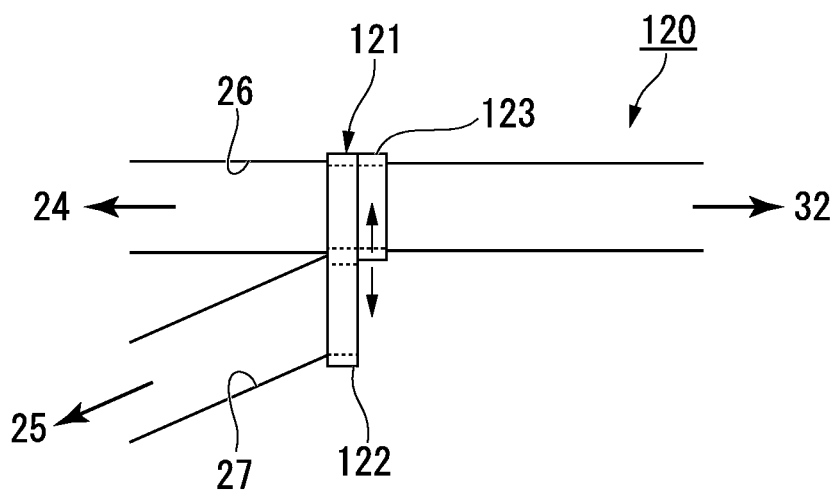
FIG. 14 is a sectional schematic view showing a process in treatment tool exchange of a treatment tool exchanging device of a third embodiment of the present invention.
Figure 15:
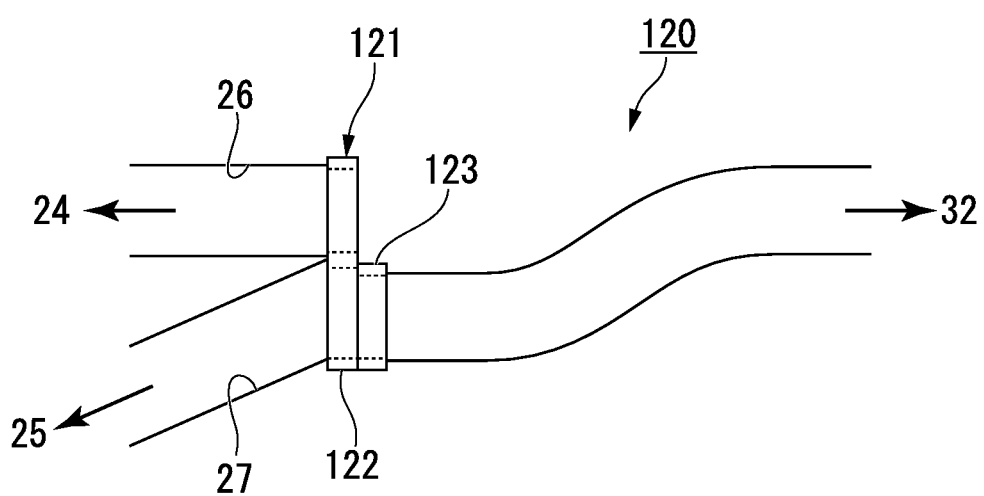
FIG. 15 is a sectional schematic view showing the process in the treatment tool exchange of the treatment tool exchanging device.

Next, a third embodiment of a treatment tool exchanging device and a medical system of the present invention will be described. FIG. 14 is a sectional schematic view showing a process in treatment tool exchange of the treatment tool exchanging device of the third embodiment of the present invention. FIG. 15 is a sectional schematic view showing the process in the treatment tool exchange of the treatment tool exchanging device.

In the present embodiment, a sliding type switching part is provided instead of the switching parts with the doors of the first embodiment.

As shown in FIG. 14, a treatment tool exchanging device 120 has a treatment tool exchange part 121. The treatment tool exchange part 121 has a sliding switching part 122 capable of respectively and independently communicating with a proximal end part of the right treatment tool channel 26 leading to the right arm 24, and a proximal end part of the left treatment tool channel 27 leading to the left arm 25. A switching channel 123 from the right treatment tool port 32 is attached to the sliding switching part 122.

As shown in FIG. 15, the treatment tool exchange part 121 can be connected to communicate with the switching channel 123 from the right treatment tool port 32 to the right treatment tool channel 26 leading to the right arm 24 by switching the sliding switching part 122. Similarly, the switching channel 123 from the right treatment tool port 32 can be connected to communicate with the left treatment tool channel 27 leading to the left arm 25 by switching the sliding switching part 122.

In the present embodiment, an end surface of the switching channel 123 can be matched with an end surface of the right treatment tool channel 26 leading to the right arm 24 or an end surface of the left treatment tool channel 27 leading to the left arm 25 by the sliding switching part 122. Therefore, the respective treatment tools 29 and 31 can be advanced and retracted without being caught.

Fourth Embodiment

Figure 16:
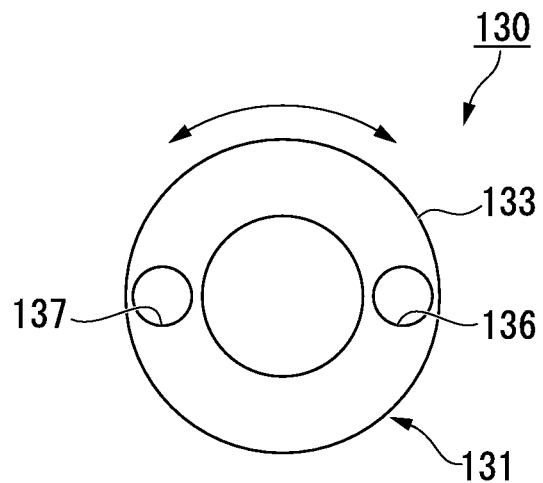
FIG. 16 is a sectional view of main parts of a treatment tool exchanging device of a fourth embodiment of the present invention.
Figure 17:
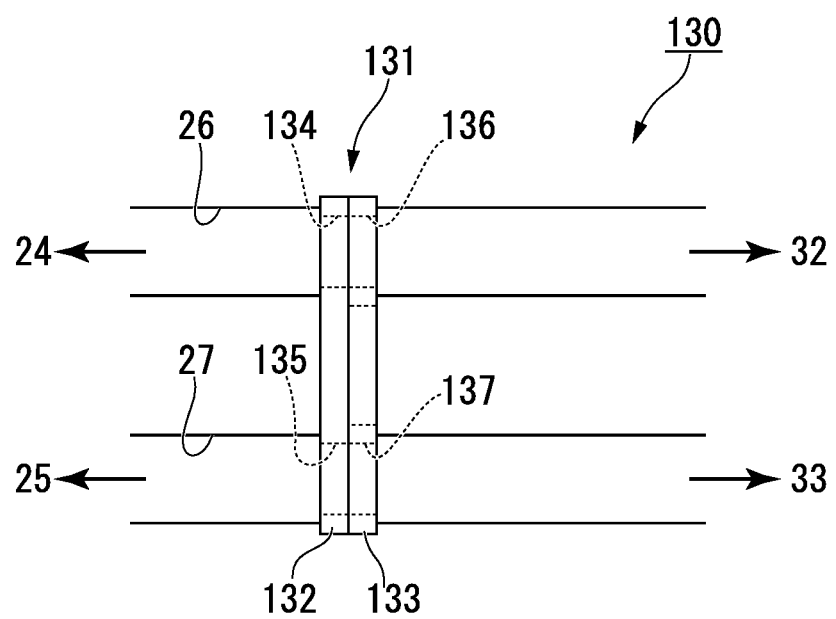
FIG. 17 is a sectional schematic view showing a process in treatment tool exchange of the treatment tool exchanging device.
Figure 18:
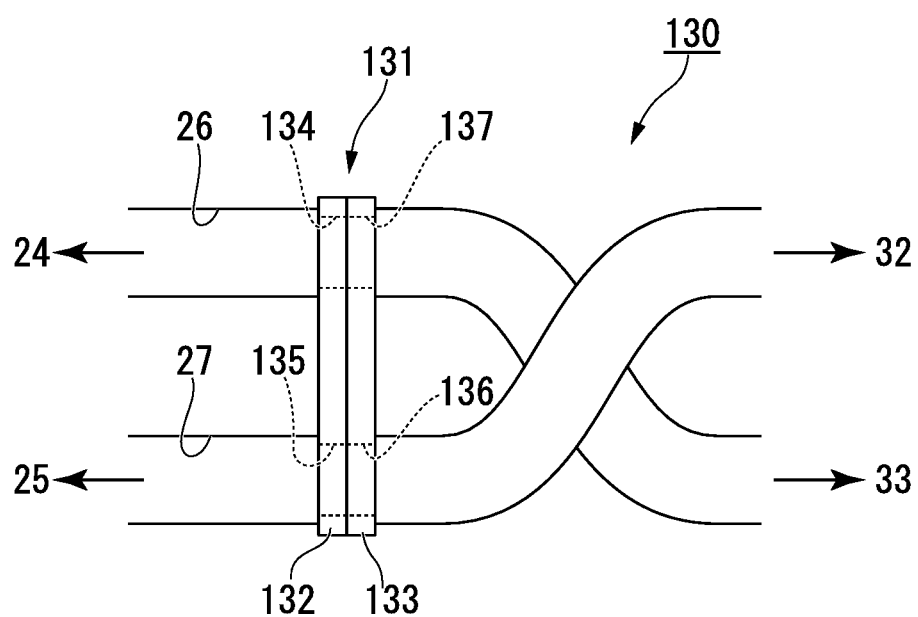
FIG. 18 is a sectional schematic view showing the process in the treatment tool exchange of the treatment tool exchanging device.

Next, a fourth embodiment of a treatment tool exchanging device and a medical system of the present invention will be described. FIG. 16 is a sectional view of main parts of the treatment tool exchanging device of the fourth embodiment of the present invention. FIG. 17 is a sectional schematic view showing a process in treatment tool exchange of the treatment tool exchanging device. FIG. 18 is a sectional schematic view showing the process in the treatment tool exchange of the treatment tool exchanging device.

In the present embodiment, a rotary switching part is provided instead of the sliding type switching part of the third embodiment.

As shown in FIG. 16, a treatment tool exchanging device 130 has a rotary switching part 131. The rotary switching part 131 includes a substrate (refer to FIG. 17) 132 and a rotary plate 133. The substrate 132 is attached to the proximal end part of the right treatment tool channel 26 and the proximal end part of the left treatment tool channel 27. The substrate 132 has a right treatment tool channel communication hole 134 that communicates with the right treatment tool channel 26, and a left treatment tool channel communication hole 135 that communicates with the left treatment tool channel 27. The rotary plate 133 is formed in an annular shape, and has a first communication hole 136 and a second communication hole 137 at positions opposite to each other by 180 degrees on the circumference. The rotary plate 133 is attached to the substrate 132 so as to be rotatable around one axis with respect to the substrate 132. In a state shown in FIG. 17, the rotary plate 133 is adapted such that the first communication hole 136 communicates with the right treatment tool channel communication hole 134 of the substrate 132, and the second communication hole 137 communicates with the left treatment tool channel communication hole 135 of the substrate 132. Therefore, the right treatment tool port 32 is connected to communicate with the right treatment tool channel 26, and the left treatment tool port 33 is connected to communicate with the left treatment tool channel 27.

As shown in FIG. 17, the rotary plate 133 rotates from the state shown in FIG. 17. Through the rotation of the rotary plate 133, the first communication hole 136 communicates with the left treatment tool channel communication hole 135 of the substrate 132, and the second communication hole 137 communicates with the right treatment tool channel communication hole 134 of the substrate 132. Therefore, the right treatment tool port 32 is connected to communicate with the left treatment tool channel 27, and the right treatment tool port 32 is connected to communicate with the right treatment tool channel 26.

In the present embodiment, whether the right treatment tool port 32 is connected to communicate with the right treatment tool channel 26 or is connected to communicate with the left treatment tool channel 27 can be simply switched by the one-axis rotation of the rotary switching part 131. Additionally, whether the left treatment tool port 33 is connected to communicate with the left treatment tool channel 27 or is connected to communicate with the right treatment tool channel 26 can be simply switched.

Additionally, in the present embodiment, the end surface of the right treatment tool channel 26 and the end surface of the left treatment tool channel 27 can be matched with an end surface on the right treatment tool port 32 side or an end surface on the left treatment tool port 33 side. Therefore, the respective treatment tools 29 and 31 can be advanced and retracted without being caught.

Fifth Embodiment

Figure 19:
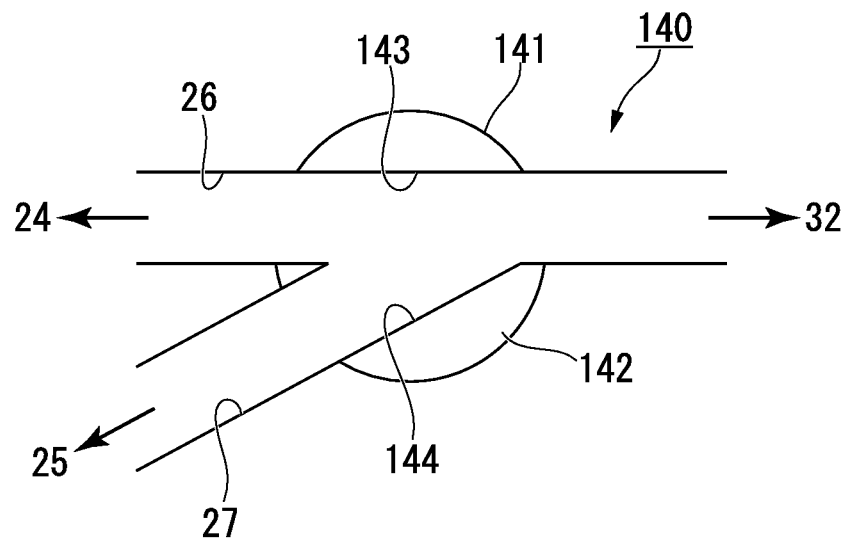
FIG. 19 is a sectional schematic view showing a process in treatment tool exchange of a treatment tool exchanging device of a fifth embodiment of the present invention.
Figure 20:
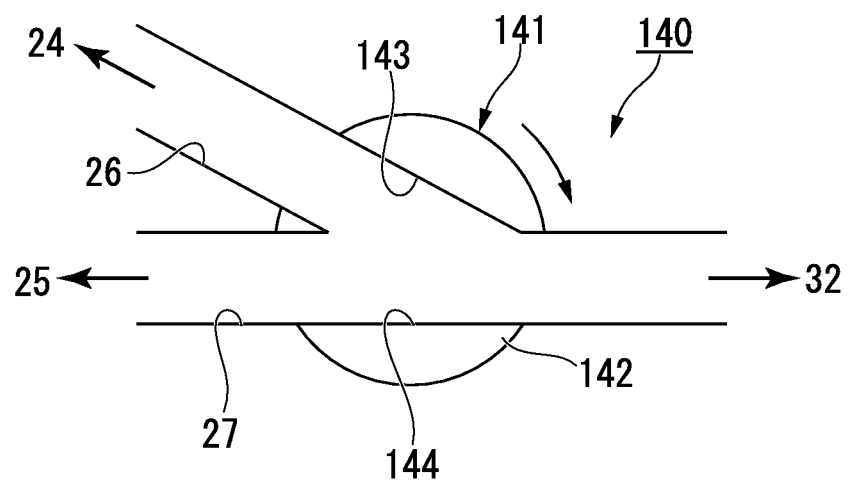
FIG. 20 is a sectional schematic view showing the process in the treatment tool exchange of the treatment tool exchanging device.

Next, a fifth embodiment of a treatment tool exchanging device and a medical system of the present invention will be described. FIG. 19 is a sectional schematic view showing a process in treatment tool exchange of the treatment tool exchanging device of the fifth embodiment of the present invention. FIG. 20 is a sectional schematic view showing the process in the treatment tool exchange of the treatment tool exchanging device.

In the present embodiment, a channel bending type switching part is provided instead of the rotating type switching part of the fourth embodiment.

As shown in FIG. 19, a treatment tool exchanging device 140 has a channel switching part 141. The channel switching part 141 includes a rotary channel member 142 having a communication tube 143 and a communication tube 144. In a state shown in FIG. 19, the right treatment tool port 32 and the right treatment tool channel 26 leading to the right arm 24 are arranged to face the communication tube 143 of the rotary channel member 142. Additionally, the communication tube 144 of the rotary channel member 142 communicates with the left treatment tool channel 27. Therefore, the right treatment tool port 32 and the right treatment tool channel 26 at the facing positions are connected to communicate with each other.

As shown in FIG. 20, the rotary channel member 142 is rotated clockwise by about 45 degrees with the center of the circle of the rotary channel member 142 as a rotation axis from a state shown in FIG. 19. If the rotary channel member 142 is rotated, the communication tubes 143 and 144 fixed to the rotary channel member 142 are moved and deformed together with the rotary channel member 142. Accordingly, the right treatment tool port 32 and the left treatment tool channel 27 leading to the left arm 25 are arranged to face the communication tube 144. Additionally, the communication tube 143 of the rotary channel member 142 communicates with the right treatment tool channel 26 leading to the right arm 24. Therefore, the right treatment tool port 32 and the left treatment tool channel 27 at the facing positions are connected to communicate with each other. Since a treatment tool that has entered from a treatment tool port has a property of moving straight ahead, the treatment tool advances into a channel at a facing position. Hence, when the right treatment tool channel 26 faces a treatment tool as shown in FIG. 19, the treatment tool is inserted into the right arm 24, and when the left treatment tool channel 27 faces a treatment tool as shown in FIG. 20, the treatment tool is inserted into the left arm 25.

In the present embodiment, whether the right treatment tool port 32 is connected to communicate with the right treatment tool channel 26 or is connected to communicate with the left treatment tool channel 27 can be simply switched by the simple operation of rotating the rotary channel member 142 together with the respective treatment tool channels 26 and 27.

While the preferred embodiments of the present invention have been described and shown above, it should be understood that these are exemplary of the present invention and are not to be considered as limiting. Additions, omissions, substitutions, and other modifications of components can be made without departing from the concept of the present invention.

For example, only one treatment tool can be switched instead of a case where the right treatment tool and the left treatment tool are switched. In that case, the right treatment tool may be inserted through the left arm after the right treatment tool is exchanged with another when the right treatment tool is inserted through the right arm and the left treatment tool is not inserted. Although an example where so-called remote control is performed by the master input unit 11 is taken and described as the manipulating part that manipulates the plurality of treatment tools, the present invention is not limited. A manipulating part may be integrally provided on a proximal end side of a driving part a treatment tool.

The invention claimed is:

1. A treatment tool exchanging device that switches and holds a plurality of treatment tools for treating a target to be treated, the treatment tool exchanging device comprising:

a flexible insertion part in which a plurality of treatment tool channels are formed, wherein the plurality of treatment tools are inserted into the plurality of treatment tool channels and the plurality of treatment tool channels define insertion paths for the treatment tools;

a driving part which advances each of the plurality of treatment tools, that are inserted through the treatment tool channels, within the treatment tool channel, and retracts each of the plurality of treatment tools within the treatment tool channel;

a manipulating part which manipulates the plurality of treatment tools and treats the target; and a control unit which controls an amount of protrusion from the treatment tool channel of the treatment tool in the state where the treatment tool protrudes from a distal end of the treatment tool channel among the plurality of treatment tools, wherein the insertion part has a switching part that changes the insertion path of the treatment tool to be inserted.

2. The treatment tool exchanging device according to claim 1, wherein the switching part includes:

a communication channel that allow the plurality of treatment tool channels to communicate with each other; and a door that closes at least one of the plurality of treatment tool channels and guides the treatment tool to at least one of the remaining treatment tool channels that are not closed.

3. The treatment tool exchanging device according to claim 1, wherein the switching part includes:

a communication channel that allows the plurality of treatment tool channels to communicate with each other;

a door that closes at least one of the plurality of treatment tool channels and guides the treatment tool to at least one of the remaining treatment tool channels that are not closed, and a path length adjusting part that adjusts a path length of the treatment tool channel.

4. A medical system comprising:

the treatment tool exchanging device according to claim 1;

a manipulator that actuates the treatment tool exchanging device; and a master input unit that performs manipulation input for giving an instruction on the operation of the treatment tool exchanging device and the manipulator.

* * * * *